United States Patent
Brugmans et al.

(10) Patent No.: US 11,864,513 B2
(45) Date of Patent: *Jan. 9, 2024

(54) DOWNY MILDEW RESISTANT LETTUCE PLANTS

(71) Applicant: Seminis Vegetable Seeds, Inc., St. Louis, MO (US)

(72) Inventors: Bart Willem Brugmans, Beek en Donk (NL); Gerard N. Koorevaar, Ede (NL); Hieronymus J. M. van der Laan, Wageningen (NL); Rosa I. Weber, Wageningen (NL)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/370,919

(22) Filed: Jul. 8, 2021

(65) Prior Publication Data

US 2022/0000054 A1  Jan. 6, 2022

Related U.S. Application Data

(63) Continuation of application No. 16/556,856, filed on Aug. 30, 2019, now Pat. No. 11,071,269, which is a continuation of application No. 15/253,573, filed on Aug. 31, 2016, now Pat. No. 10,448,595.

(60) Provisional application No. 62/214,097, filed on Sep. 3, 2015.

(51) Int. Cl.
| | |
|---|---|
| *A01H 6/14* | (2018.01) |
| *C12N 15/82* | (2006.01) |
| *A01H 1/04* | (2006.01) |
| *A01H 5/12* | (2018.01) |
| *C12Q 1/6895* | (2018.01) |

(52) U.S. Cl.
CPC .......... *A01H 6/1472* (2018.05); *A01H 1/045* (2021.01); *A01H 5/12* (2013.01); *C12N 15/82* (2013.01); *C12Q 1/6895* (2013.01); *C12Q 2600/13* (2013.01); *C12Q 2600/156* (2013.01); *C12Q 2600/158* (2013.01)

(58) Field of Classification Search
CPC .................................................. A01H 6/1472
See application file for complete search history.

(56) References Cited

U.S. PATENT DOCUMENTS 10,448,595 B2 * 10/2019 Brugmans ............ A01H 6/1472
11,071,269 B2 *  7/2021 Brugmans ............ C12Q 1/6895

FOREIGN PATENT DOCUMENTS

EP      2272328 A1    1/2011

OTHER PUBLICATIONS

Bonnier et al., "New sources of major gene resistance in *Lactuca* to *Bremia lactucae*," *Euphytica*, 61:203-211, 1992.
Gustafsson, "Potential sources of resistance to lettuce downy mildew (*Bremia lactucae*) in different *Lactuca* species," *Euphytica*, 40:227-232, 1989.
Lebeda et al., "Histological characterization of resistance in *Lactuca saligna* to lettuce downy mildew (*Bremia lactucae*)," *Physiol Mol Plant Pathol*, 44(2):125-139, 1994.
Lebeda et al., "Wild *Lactuca* species, their genetic diversity, resistance to diseases and pests, and exploitation in lettuce breeding," *Eur J Plant Pathol*, 138:597-640, 2014.
Jeuken et al., "Efficient QTL detection for nonhost resistance in wild lettuce: backcross inbred lines versus $F_2$ population," *Theor. Appl. Genet.* 116:845-857, 2008.
Maisonneuve, "*Lactuca virosa*, a source of disease resistance genes for lettuce breeding: results and difficulties for gene introgression," EUCARPIA Leafy Vegetables Conference, 2003.
McHale et al., "The genomic architecture of disease resistance in lettuce," Theor Appl Genet, 118:565-580, 2009.
Netzer, "*Lactuca saligna* L., a new source of resistance to downy mildew (*Bremia lactucae* Reg.) [Lettuce, fungal diseases]," *HortScience*, 11:612-613, 1976.
Truco et al., "An ultra-high density, transcript-based, genetic map of lettuce," *G3 (Bethesda)*, 3:617-631, 2013.
Extended European Search Report regarding European Application No. 16186958.1, dated Feb. 8, 2017.

\* cited by examiner

*Primary Examiner* — Brent T Page
(74) *Attorney, Agent, or Firm* — Dentons US LLP; Michelle Samonek

(57) ABSTRACT

The present disclosure provides lettuce plants exhibiting resistance to downy mildew. Such plants may comprise novel introgressed genomic regions associated with disease resistance from *L. virosa*. In certain aspects, compositions, including novel polymorphic markers and methods for producing, breeding, identifying, and selecting plants or germplasm with a disease resistance phenotype are provided.

5 Claims, 2 Drawing Sheets

Specification includes a Sequence Listing.

FIG. 2

NLSAT005132975 DNA sequence
CTCTACCGATGGTGATAATCCGCCTTTTGATTTTGGGATTTTTNAACAGGCNTTNTCN
TCGGGGATTGTTTCTTCNAAAAANTTTGTTTCAAAGTACTGTTATTGCCTCTGGTGGG
GCCT[A/G]CAGAATTTGAGGTATATAACNATATTCTATATNTATTTNTTTTNAG
G= *L. virosa* allele
A= *L. sativa* allele

NLSAT009419770 DNA sequence
AGGCTCAAGTAGAGGGATTGAAGAAGNAAAACTGGAAGATCNAGCANATTAGAGG
GCATATTTCTTTGTTTGTCAGAGANAGTNGNGGATTGTTGANGCANTGTGGTAGGGT
TTAGGNTNCNGNGTCAGNTGNGGTGAGACANANGNATTTAGAAGAGGNNCANAAA
TCCAAGTTTTCTCTCNATTNGGGGGCTACGAAGATGTAC[C/T]GAGATTTGAGATTGA
GTTACTGGTGGCCCTGTATGAAAAGGGA
T = *L. virosa* allele
C = *L. sativa* allele

ND0229340 DNA sequence
TCGAAGACGGGTGAACTACNCGCCTGATTAGTGTCTATTTCTTTTACTTTGNAATNTA
CANAAGNATTTCGTNGAACAGATGGCNGGNGAAGACAGAAACAA[C/T]GGCGTCCT
ACATNGANANTACNAGCTTGNTCGGNAGCTAGGTCACGGCACNTTTGCGAA
C= *L. virosa* allele
T= *L. sativa* allele

SEQUENCE LISTING

```
<160> NUMBER OF SEQ ID NOS: 15

<210> SEQ ID NO 1
<211> LENGTH: 167
<212> TYPE: DNA
<213> ORGANISM: Lactuca sativa
```

<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 1
ctctaccgat ggtgataatc cgccttttga ttttgggatt tttnaacagg cnttntcntc        60
ggggattgtt tcttcnaaaa antttgtttc aaagtactgt tattgcctct ggtggggcct       120
rcagaatttg aggtatataa cnatattcta tatntatttn ttttnag                     167

<210> SEQ ID NO 2
<211> LENGTH: 22
<212> TYPE: DNA
<213> ORGANISM: Artificial sequence
<220> FEATURE:
<223> OTHER INFORMATION: Primer

<400> SEQUENCE: 2
cccaccagag gcaataacag ta                                                 22

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
cgatggtgat aatccgcctt ttgat                                              25

<210> SEQ ID NO 4
<211> LENGTH: 18
<212> TYPE: DNA
<213> ORGANISM: Artificial sequence
<220> FEATURE:

-continued

<223> OTHER INFORMATION: Probe

<400> SEQUENCE: 4
ctttgaaaca aaattttt                                                       18

<210> SEQ ID NO 5
<211> LENGTH: 18
<212> TYPE: DNA
<213> ORGANISM: Artificial sequence
<220> FEATURE:
<223> OTHER INFORMATION: Probe

<400> SEQUENCE: 5
ctttgaaaca aacttttt                                                       18

<210> SEQ ID NO 6
<211> LENGTH: 250
<212> TYPE: DNA
<213> ORGANISM: Lactuca sativa
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t

```
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (160)..(161)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 6
aggctcaagt agagggattg aagaagnaaa actggaagat cnagcanatt agagggcata     60
tttctttgtt tgtcagagan agtngnggat tgttgangca ntgtggtagg gtttaggntn    120
cngngtcagn tgnggtgaga canangnatt tagaagaggn ncanaaatcc aagttttctc    180
tcnattnggg ggctacgaag atgtacygag atttgagatt gagttactgg tggccctgta    240
tgaaaaggga                                                          250

<210> SEQ ID NO 7
<211> LENGTH: 27
<212> TYPE: DNA
<213> ORGANISM: Artificial sequence
<220> FEATURE:
<223> OTHER INFORMATION: Primer

<400> SEQUENCE: 7
agggcatatt tctttgtttg tcagaga                                        27

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
cagggccacc agtaactca                                                 19

<210> SEQ ID NO 9
<211> LENGTH: 20
<212> TYPE: DNA
<213> ORGANISM: Artificial sequence
<220> FEATURE:
<223> OTHER INFORMATION: Probe

<400> SEQUENCE: 9
atctcaaatc tcggtacatc                                                20

<210> SEQ ID NO 10
```

```
<211> LENGTH: 20
<212> TYPE: DNA
<213> ORGANISM: Artificial sequence
<220> FEATURE:
<223> OTHER INFORMATION: Probe

<400> SEQUENCE: 10
atctcaaatc tcagtacatc                                              20

<210> SEQ ID NO 11
<211> LENGTH: 162
<212> TYPE: DNA
<213> ORGANISM: Lactuca sativa
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t

<400> SEQUENCE: 11
tcgaagacgg gtgaactacn cgcctgatta gtgtctattt cttttacttt gnaatntaca     60
```

```
naagnatttc gtngaacaga tggcnggnga agacagaaac aayggcgtcc tacatngana      120
ntacnagctt gntcggnagc taggtcacgg cacntttgcg aa                        162

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
gaacagatgg caggtgaaga ca                                              22

<210> SEQ ID NO 13
<211> LENGTH: 23
<212> TYPE: DNA
<213> ORGANISM: Artificial sequence
<220> FEATURE:
<223> OTHER INFORMATION: Primer

<400> SEQUENCE: 13
ccgaccaagc tcgtattttc cat                                             23

<210> SEQ ID NO 14
<211> LENGTH: 16
<212> TYPE: DNA
<213> ORGANISM: Artificial sequence
<220> FEATURE:
<223> OTHER INFORMATION: Probe

<400> SEQUENCE: 14
taggacgcca ttgttt                                                     16

<210> SEQ ID NO 15
<211> LENGTH: 16
<212> TYPE: DNA
<213> ORGANISM: Artificial sequence
<220> FEATURE:
<223> OTHER INFORMATION: Probe

<400> SEQUENCE: 15
taggacgccg ttgttt                                                     16
```

US 11,864,513 B2

DOWNY MILDEW RESISTANT LETTUCE PLANTS

CROSS-REFERENCE TO RELATED APPLICATIONS

This application is a continuation of U.S. application Ser. No. 16/556,856, filed Aug. 30, 2019, which is a continuation of U.S. application Ser. No. 15/253,573, filed Aug. 31, 2016, now U.S. Pat. No. 10,448,595, which claims the priority of U.S. Provisional Appl. Ser. No. 62/214,097, filed Sep. 3, 2015, the entire disclosures of which are incorporated herein by reference in their entireties.

FIELD OF THE INVENTION

The present invention relates to the field of agriculture and more specifically to methods and compositions for producing lettuce plants exhibiting improved disease resistance.

INCORPORATION OF SEQUENCE LISTING

The sequence listing that is contained in the file named "SEMB018US_ST25.txt", which is 6.83 kilobytes as measured in Microsoft Windows operating system and was created on Aug. 31, 2016, is filed electronically herewith and incorporated herein by reference.

BACKGROUND OF THE INVENTION

Disease resistance is an important trait in agriculture, particularly for the production of food crops. Although disease resistance alleles have been identified in wild lettuce lines, efforts to introduce these alleles into cultivated lines are hindered by a lack of specific markers linked to the alleles, linkage drag that leads to unacceptable plant quality and a lack of durable resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, and an often incomplete understanding of the genetic background underlying expression of a desired phenotype.

SUMMARY OF THE INVENTION

In one aspect, the present invention provides an elite lettuce plant comprising an introgression from *Lactuca virosa* on chromosome 7, wherein said introgression comprises a single gene conferring improved resistance to *Bremia lactucae* relative to a plant lacking said introgression.

In another aspect, the present invention provides an elite lettuce plant comprising an introgression from *Lactuca virosa* on chromosome 7, wherein said introgression comprises a first allele conferring improved resistance to *Bremia lactucae* relative to a plant lacking said introgression, and wherein said introgression lacks a second allele genetically linked to said first allele and conferring stunted growth. In some embodiments, the introgression from *Lactuca virosa* is located between 53.6 Mb and 55.2 Mb. In other embodiments, the introgression comprises a first allele at position 53,628,734 bp conferring improved resistance to *Bremia lactucae* relative to a plant lacking said first allele, and wherein said introgression lacks a second allele genetically linked to said first allele at position 55,223,518 bp. In further embodiments, the introgression from *Lactuca virosa* is about 250 kb or less. The invention further provides an elite lettuce plant comprising a *Lactuca virosa* allele at locus NLSAT009419770, and wherein the plant lacks a *Lactuca virosa* allele at locus ND0229340 or NLSAT005132975. In specific embodiments, the plant comprises a *Lactuca virosa* allele at locus NLSAT009419770 (SEQ ID NO: 6) and a *Lactuca sativa* allele at locus NLSAT005132975 (SEQ ID NO:1), or is defined as comprising a *Lactuca virosa* allele at locus NLSAT009419770 (SEQ ID NO: 6) and a *Lactuca sativa* allele at locus ND0229340 (SEQ ID NO: 11). In certain additional embodiments, the invention provides an introgression, wherein a sample of seed comprising the introgression was deposited under ATCC Accession Number PTA-121598. In further embodiments, the invention provides a plant part of a lettuce plant of the invention, wherein the plant part is a cell, a seed, a root, a stem, a leaf, a head, a flower, or pollen.

In a further aspect, the invention provides a method for producing a lettuce plant with improved resistance to *Bremia lactucae*, comprising: a) crossing an elite lettuce plant of the invention with itself or with a second lettuce plant of a different genotype to produce one or more progeny plants; and b) selecting a progeny plant comprising said introgression. In some embodiments, selecting the progeny plant comprises identifying a progeny plant that (1) comprises a *Lactuca virosa* allele at a locus genetically linked to said first allele and/or lacks an elite allele present at the corresponding locus in the elite lettuce plant, and (2) lacks a *Lactuca virosa* allele at a locus genetically linked to said second allele, and/or comprises an allele present at the corresponding locus from in the elite lettuce plant. In further embodiments, selecting a progeny plant comprises detecting at least one allele at a locus selected from the group consisting of NLSAT009419770, ND0229340 and NLSAT005132975. In certain embodiments, the allele(s) are detected by a PCR-based method using oligonucleotide primer pair(s); and the allele at locus NLSAT009419770 is detected using the primer pair comprising SEQ ID NO: 7 and SEQ ID NO: 8; or the allele at locus ND0229340 is detected using the primer pair comprising SEQ ID NO: 12 and SEQ ID NO: 13; or the allele at locus NLSAT005132975 is detected using the primer pair comprising SEQ ID NO: 2 and SEQ ID NO:3. In certain other embodiments, selecting a progeny plant comprises detecting an allele at locus NLSAT009419770 and an allele at locus ND0229340. The progeny plant may be an F2-F6 progeny plant. Producing the progeny plant may comprise backcrossing, for example between 2-7 generations of backcrosses. In further embodiments, a sample of seed comprising said introgression was deposited under ATCC Accession Number PTA-121598.

In yet another aspect, the invention provides a method for obtaining an elite lettuce plant exhibiting improved resistance to *Bremia lactucae*, comprising: a) obtaining an elite lettuce plant heterozygous for a first allele from *Lactuca virosa* that confers quantitative resistance to *Bremia lactucae* and that is genetically linked in the plant to a second allele from *Lactuca virosa* that confers stunted growth, wherein the plant is heterozygous relative to a corresponding locus in said elite plant; (b) obtaining progeny of the plant; and (c) selecting at least a first progeny plant in which recombination has occurred such that the progeny comprises said first allele that confers quantitative resistance to *Bremia lactucae* but not said second allele. In some embodiments, selecting the progeny plant comprises identifying a progeny plant that comprises a *Lactuca virosa* allele at a locus genetically linked to said first allele and/or lacks an allele present at the corresponding locus in the elite lettuce plant, and lacks a *Lactuca virosa* allele at a locus genetically linked to said second allele, and/or comprises an allele present at the corresponding locus from in the elite lettuce plant. In other embodiments, selecting a progeny plant comprises detecting at least one allele at a locus selected from the group consisting of NLSAT009419770, ND0229340 and NLSAT005132975. In further embodiments, (a) the allele(s) are detected by a PCR-based method using oligonucleotide primer pair(s); and (b) the allele at locus NLSAT009419770 is detected using the primer pair comprising SEQ ID NO: 7 and SEQ ID NO: 8; or the allele at locus ND0229340 is detected using the primer pair comprising SEQ ID NO: 12 and SEQ ID NO: 13; or the allele at locus NLSAT005132975 is detected using the primer pair comprising SEQ ID NO: 2 and SEQ ID NO:3. In certain embodiments, selecting a progeny plant comprises detecting an allele at locus NLSAT009419770 and an allele at locus ND0229340. Further embodiments provide a plant produced by the methods of the invention, for example a cell, a seed, a root, a stem, a leaf, a head, a flower, and pollen.

In another aspect, the invention provides an elite lettuce plant, wherein a sample of seed of said plant was deposited under ATCC Accession Number PTA-121598.

In yet another aspect, the invention provides a method for producing a lettuce plant with improved resistance to *Bremia lactucae*, comprising: a) crossing an elite lettuce plant wherein a sample of seed of said plant was deposited under ATCC Accession Number PTA-121598 with itself or with a second lettuce plant of a different genotype to produce one or more progeny plants; and b) selecting a progeny plant comprising an introgression from *Lactuca virosa* on chromosome 7, wherein said introgression comprises a first allele conferring improved resistance to *Bremia lactucae* relative to a plant lacking said first allele, and wherein said introgression lacks a second allele genetically linked to said first allele and conferring stunted growth. In certain embodiments, selecting a progeny plant comprises detecting at least one allele at a locus selected from the group consisting of NLSAT009419770, ND0229340 and NLSAT005132975. In other embodiments, (a) the allele(s) are detected by a PCR-based method using oligonucleotide primer pair(s); and (b) the allele at locus NLSAT009419770 is detected using the primer pair comprising SEQ ID NO: 7 and SEQ ID NO: 8; or the allele at locus ND0229340 is detected using the primer pair comprising SEQ ID NO: 12 and SEQ ID NO: 13; or the allele at locus NLSAT005132975 is detected using the primer pair comprising SEQ ID NO: 2 and SEQ ID NO:3. In further embodiments, selecting a progeny plant comprises detecting an allele at locus NLSAT009419770 and an allele at locus ND0229340. The invention further provides a plant produced by the methods of the invention.

In certain embodiments, the invention provides a marker for identifying a plant with improved resistance to *Bremia lactucae* selected from the group consisting of NLSAT005132975 (SEQ ID NO:1), NLSAT009419770 (SEQ ID NO: 6), and ND0229340 (SEQ ID NO: 11). In one embodiment, the marker comprises NLSAT005132975 (SEQ ID NO:1), or NLSAT009419770 (SEQ ID NO: 6), or ND0229340 (SEQ ID NO: 11). In other embodiments, more than one or all three markers may be used. In further embodiments, a marker linked to or associated with any of the markers described herein may be useful in accordance with the invention. For example, such a marker may be located within 40 cM, 20 cM, 15 cM, 10 cM, 5 cM, 2 cM, or 1 cM of a marker associated with disease resistance described herein. In other embodiments, a marker in accordance with the invention may comprise 100% sequence identity or homology to a marker described herein, or may comprise 95%, 90%, 85%, 80%, 75%, 70%, 65%, 60%, 55%, 50% sequence identity or homology to a marker described herein. In still further embodiments, a marker useful with the invention may be comprised within a plant genome, such as a lettuce plant.

BRIEF DESCRIPTION OF THE DRAWINGS

FIG. 2: Shows marker sequences NLSAT009419770 (SEQ ID NO: 6), ND0229340 (SEQ ID NO: 11) and NLSAT005132975 (SEQ ID NO:1). Polymorphic nucleotides between *L. virosa* and *L. sativa* are indicated.

DETAILED DESCRIPTION

Figure 1A:
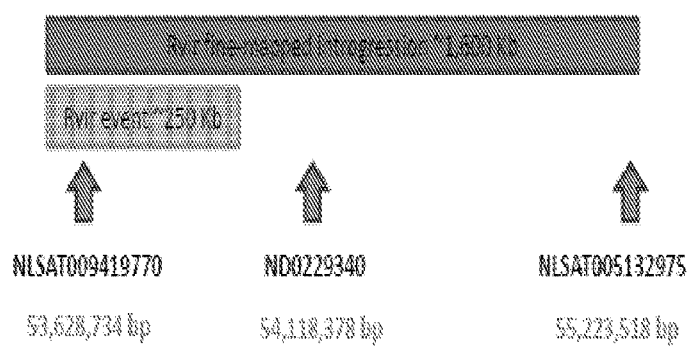
FIG. 1A and FIG. 1B: Shows a physical map of a *Lactuca virosa* introgression segment and the positions of markers used for recombination screenings.

Downy mildew (DM) is a damaging fungal disease caused by *Bremia lactucae*, which can result in severe crop loss in lettuce plants (*Lactuca sativa*). Several wild lettuce species, including *Lactuca serriola* and *Lactuca virosa*, are known to exhibit resistance to DM, and intensive efforts have been made to introgress DM resistance alleles from these species into cultivated lettuce types. However, these efforts have been unsuccessful in producing commercially acceptable lettuce with resistance to DM. The previously known alleles have failed to provide reproducible results, provide durable DM resistance or have been accompanied by undesirable agronomic traits. Downy mildew remains a leading cause of crop loss in lettuce.

The present invention provides novel introgressions of disease resistance alleles from *Lactuca virosa*. These alleles can be introgressed into cultivated lettuce lines, resulting in lettuce plants which exhibit DM resistance. In addition, these novel introgressions are smaller fragments from the wild species and therefore also have a reduced risk of linked, deleterious traits or linkage drag. The invention represents a significant advance in the art. The invention further provides novel markers for tracking the genomic segments. The novel fragment can be used to introgress DM disease resistance into any desired lettuce genotype.

Resistance to downy mildew has been obtained with introgressions from the wild lettuce *Lactuca serriola*, which can be successfully crossed with cultivated lettuce types and generally does not have significant linkage drag. However, the *B. lactucae* pathogen is highly genetically variable, and has rapidly adapted to the resistance alleles which have been found in *L. serriola*. As such, there is an ongoing need for the identification of new resistance alleles to target the new isolates of the pathogen. The development of new alleles is costly and laborious. To date, *L. serriola* has not provided durable DM resistance.

The wild lettuce *L. virosa* has provided a durable source of resistance to *Nasonovia ribisnigri* race 0 that has lasted for many years. However, to date, the resistance alleles to DM from *L. virosa* which have been described have not succeeded in providing durable resistance. In addition, the DM resistance alleles from *L. virosa* have required the presence of two or more genes, have resulted in significant linkage drag and/or have not been able to be successfully reproduced or successfully incorporated into cultivated lettuce for resistance. *L. virosa* is also difficult to cross with cultivated lettuce lines and the progeny plants generally exhibit severe linkage drag effects as a result of the presence of an *L. virosa* introgression.

Prior efforts to introgress DM resistance alleles from *L. virosa* have not been successful in providing commercially acceptable lettuce plants with resistance to DM. The prior efforts have not been reproducible, have provided relatively large introgressions with significant linkage drag and/or have required the presence of multiple genes. The larger introgressions from *L. virosa* exacerbate the deleterious traits typically observed with *L. virosa*. Introgression of any alleged *L. virosa* DM resistance alleles has also been complicated by a lack of markers and assays that accurately correlate genotype with resistance over a variety of lettuce lines. The use of markers in developing lettuce lines with resistance to DM from *L. virosa* has been hindered by a lack of predictive markers. The previously reported markers for identifying or tracking DM resistance in lettuce plants could not be reproduced. Moreover, previously identified markers are not predictive across multiple plant lines, or are not tightly linked to DM resistance loci and are therefore ineffective when disease resistance is crossed into a related species. For example, the use of random amplified polymorphic DNA (RAPD) assays for the identification and tracking of DM resistance and lettuce plants has been found not to be reproducible (Jones, et al., 1997, *Molecular Breeding* 3:381-390), and previously reported RAPD markers are not reliably useful in detecting a given resistance gene in different plant populations (Kelly, et al., 1995, *HortScience* 30:461-465).

Despite the many obstacles to the successful introgression of *L. virosa* resistance alleles into cultivated lettuce lines, the present inventors were able to produce novel introgressions from *L. virosa* which confer DM resistance. These novel introgressions are smaller and lack or reduce the deleterious traits previously associated with *L. virosa* crosses. In addition, the present invention includes novel trait-linked markers which can be used to make novel recombined introgressions on chromosome 7 and confer DM resistance. The invention further identifies and provides a genomic segment from approximately 53.4 Mb to 56.1 Mb on chromosome 7 associated with DM resistance. The present invention further provides a novel introgression fragment from *L. virosa* having a size of about 250 kb or less. Surprisingly, the novel introgression results in plants exhibiting DM resistance. In addition, certain linkage drag often associated with introgressions from *L. virosa*, including stunted growth, has not been observed with the novel introgression provided herein. The novel introgression provided by the invention therefore yields lettuce plants resistant to DM while beneficially reducing or eliminating the introduction of negative agronomic traits from *L. virosa* into an elite background.

The invention further provides novel markers and assays that allow the accurate identification and tracking of the genomic regions provided herein. Because genetically diverse lettuce lines can be difficult to cross due in part to suppressed recombination, the introduction of DM resistance alleles from *L. virosa* into elite lines using conventional breeding methods would require prohibitively large segregating populations for progeny screens with an uncertain outcome. Marker-assisted selection (MAS) is therefore important for the effective introgression of wild lettuce alleles into elite cultivars. However, previously known markers for DM resistance have been shown to be non-reproducible or inaccurate, perhaps because of poor quality of the markers or a lack of understanding of the mechanisms controlling DM resistance and the inability to resolve the specific regions associated with resistance. In contrast, the present invention allows for MAS by providing improved and validated markers for detecting genotypes associated with disease resistance.

II. Genomic Regions, Alleles, and Polymorphisms Associated with Downy Mildew Resistance in Lettuce Plants DM can infect lettuce plants at any stage in the growth cycle and can cause severe reduction in yield and quality in a lettuce crop. Cultivar resistance is the most economically feasible way of controlling DM infection due the high cost of fungicide spray applications. Intensive efforts have therefore been made to identify effective sources of DM resistance. However, previously known introgressions from wild species have not produced commercially useful lettuce crops due to a lack of durable resistance or unacceptable associated deleterious traits.

Other accessions of *L. virosa* exhibiting DM resistance are known in the art and may be used in accordance with certain embodiments of the invention. It may also be possible to use other wild lettuce types including *L. serriola*, and *L. saligna*. Accessions for *L. serriola* lines exhibiting resistance to various *B. lactucae* races are given, for example, in Lebeda, et al., *Eur J Plant Pathol*, 138:597-640, 2014. *Lactuca saligna* accession CGN05271, which can be obtained from the Center for Genetic Resources (Wageningen, The Netherlands) also exhibits DM resistance. *L. virosa* exhibiting DM resistance is described in Lebeda, et al., 2014. *L. virosa* accessions have been collected in numerous locales including France and Portugal and can be found in a number of germplasm banks including Center for Genetic Resources, the Netherlands (CGN) and National Plant Germplasm System (NPGS).

Other DM resistance sources have also been described and are known in the art (see, for example, Lebeda, et al., *Molecular Plant Pathology*, 44:125-139, 1995; Bonnier, et al., *Euphytica* 61: 203-211, 1992; Gustafsson, *Euphytica*, 40: 227-232, 1989; and Netzer, *Hort. Sci.*, 11:612-613, 1976).

Efforts to introgress DM resistance into cultivated lettuce lines have also been unsuccessful or complicated by the fact that previously described introgressions have been very large or are derived from introgressions occurring at several distinct loci. In addition, previous studies have reported that two or more resistance genes from *L. virosa* are required for durable DM resistance in lettuce. However, the introduction of a large amount of genetic material by introgressing large genomic segments greatly increases the incidence of negative traits as a result of linkage drag. Despite numerous efforts, no alleles from *L. virosa* which confer durable resistance to DM have yet been discovered.

A further hindrance to the effective identification of DM resistance alleles and introgression into cultivated lettuce lines is the high genetic variability of the *B. lactucae* pathogen. The genetic adaptability of the pathogen allows it to overcome resistance derived from certain species of wild lettuce. For example, resistance alleles from *L. serriola* have been shown to be readily "broken down" by *B. lactucae*. Moreover, known *B. lactucae* resistance alleles have been shown to have varying resistance to different *B. lactucae* races.

It is therefore desirable to identify smaller genomic regions conferring DM resistance. It is also desirable to provide resistance with a single gene and to provide a gene having more durable resistance. Such smaller region may not include alleles associated with linkage drag. In addition, resistance residing in smaller introgressions or associated with a single gene is also less likely to be broken down during breeding, which results in more durable resistance. The introgression identified herein or any introgression with a reduced introgression size has not been achieved previously. Moreover, no effective markers which are closely linked to resistance have been described.

Using the genetic markers and assays of the invention, Applicants were able to successfully identify a novel DM resistance region from *L. virosa*. This region also results in a reduction or elimination of linkage drag associated with *L. virosa*. In certain embodiments, the novel introgression of the present invention spans a region defined as between about 49.8 cM and 50.5 cM on Linkage Group 7. Public markers that define Linkage Group 7 have been published by McHale (McHale et al., *Theor Appl Genet* (2009) 118:565-580) and Truco (Truco et al., 2013 G3 (2013) 3: 617-631). The genetic interval appeared to correspond to the physical interval of approximately 53.4 Mb to 56.1 Mb as determined based on a genome consensus map generated in a collaboration of the Michelmore lab at UC Davis and the BGI, Shenzen employing genome sequence data from the Lettuce Genome Sequencing Consortium (available at lgr.genomecenter.ucdavis.edu/Home.php). One of skill in the art will understand that interval values may vary based on factors such as the reference map that is used, the sequencing coverage and the assembly software settings. However, such parameters and mapping protocols are known in the art and one of skill in the art can use the marker sequences provided herein to physically and genetically anchor the introgressions described herein to any given map using such methodology.

The invention further provides a novel introgression from *L. virosa* which is much smaller than previously known introgressions, and which effectively confers resistance in an elite background. In addition, the smaller introgression reduces negative linkage drag. In some embodiments, the DM resistance locus has an introgression size of 250 kb or less. The novel introgression of the present invention therefore confers significantly improved agronomic properties over previous lettuce lines.

III. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions from *L. virosa* disclosed herein into cultivated lines. The invention further provides markers for identifying and tracking the novel introgressions disclosed herein during plant breeding, including markers NLSAT005132975 (SEQ ID NO:1), NLSAT009419770 (SEQ ID NO: 6), and ND0229340 (SEQ ID NO: 11).

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease tolerant phenotype.

Lettuce plants comprising one or more introgressed regions associated with a desired phenotype wherein at least 10%, 25%, 50%, 75%, 90%, or 99% of the remaining genomic sequences carry markers characteristic of the germplasm are also provided. Lettuce plants comprising an introgressed region comprising regions closely linked to or adjacent to the genomic regions and markers provided herein and associated with a disease resistance phenotype are also provided.

IV. Development of Disease Resistant Lettuce Varieties

For most breeding objectives, commercial breeders work within germplasm that is "cultivated type" or "elite." This germplasm is easier to breed because it generally performs well when evaluated for horticultural performance. A number of cultivated lettuce types have been developed, including *L. sativa*, which is agronomically elite and appropriate for commercial cultivation. Lettuce cultivar groups include, but are not limited to the Cos, Cutting, Stalk (or Asparagus), Butterhead, Crisphead (or Iceberg or Cabbage), Latin and Oilseed groups (De Vries, *Gen. Resources and Crop Evol.* 44: 165-174, 1997). However, the performance advantage a cultivated germplasm provides can be offset by a lack of allelic diversity. Breeders generally accept this tradeoff because progress is faster when working with cultivated material than when breeding with genetically diverse sources.

When cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In lettuce plants, non-cultivated types such as *L. serriola* or *L. virosa* can provide alleles associated with disease resistance. However, these non-cultivated types may have poor horticultural qualities.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance will facilitate the development of lettuce plants having beneficial phenotypes. For example, seed can be genotyped using the markers of the present invention in order to select for plants comprising desired genomic regions associated with disease resistance. Moreover, MAS allows identification of plants which are homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rina gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens.

Phenotypic evaluation of large populations is time-consuming, resource-intensive and not reproducible in every environment. Marker-assisted selection (MAS) offers a feasible alternative. Molecular assays designed to detect unique polymorphisms, such as SNPs, are versatile. However, they may fail to discriminate alleles within and among lettuce species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

V. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step and is not discussed here. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

In contrast to AFLP, random amplification of polymorphic DNA (RAPD) technology attacks the genome in its full complexity. Typically, a single primer of 10 nucleotides is used to amplify any fragment of the genome that, by chance, shows a pattern of tandem homology. It appears that the RAPD technology is versatile, low cost and prompt. But whether it offers a robust marker platform is debated (reviewed in Bardakci, 2001). Penner and coworkers (1993) found that RAPD amplification was inconsistent when comparing results from two oat cultivars (*Avena sativa* L.) with five primers in seven laboratories. Different size ranges of fragments were detected in each laboratory and the majority of fragments that were polymorphic between the cultivars were not amplified in all experiments. Ghazi et al. (2013) also observed both stable and conflicting bands in separate experiments, despite studying the small genome of the prokaryote *Streptococcus thermophilus*. All authors agree that minor changes in the experimental conditions of the RAPD technique influence the amplification and thus the presence of markers. The Centre of Genetic Resources in the Netherlands selectively scores RAPD markers with a position on the genetic map and a confirmed Mendelian inheritance (www.wageningenur.nl/nl/show/Characteristics-of-genetic-markers-Reproducibility.htm). The USDA (www.download.springer.com/static/pdf/290/chp%253A10.1007-%252F978-0-387-30443-4_3.pdf?auth66=1400332645_81ff70ea87777fbaeca0d6d9d1700604&ext=.pdf) argues in favor of elongating RAPD primers to enhance specificity and thereby reproducibility. Nucleotides adjacent to the primers are sequenced and added to primer design and synthesis. Such 'sequence-characterized amplified regions', or SCAR markers can be applied to study lettuce genetics. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) *EPO* 0273085), or cleavage fragment length polymorphisms (Life Technologies, Inc., Gathersberg, MD), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a lettuce plant a genotype associated with disease resistance, identify a lettuce plant with a genotype associated with disease resistance, and to select a lettuce plant with a genotype associated with disease resistance. In certain embodiments of methods of the invention, polymorphic nucleic acids can be used to produce a lettuce plant that comprises in its genome an introgressed locus associated with disease resistance. In certain embodiments of the invention, polymorphic nucleic acids can be used to breed progeny lettuce plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in lettuce plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite line" or "cultivated line" means any line that has resulted from breeding and selection for superior agronomic performance. An "elite plant" refers to a plant belonging to an elite line. Numerous elite lines are available and known to those of skill in the art of lettuce breeding. An "elite population" is an assortment of elite individuals or lines that can be used to represent the state of the art in terms of agronomically superior genotypes of a given crop species, such as lettuce. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility for downy mildew.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 2500 seeds of lettuce line CHCG413-0099, which comprises an introgression from *L. virosa*, as described herein. The deposit was made with the American Type Culture Collection (ATCC), 10801 University Boulevard, Manassas, Va. 20110-2209 USA. The deposit is assigned ATCC Accession No. PTA-121598, and the date of deposit was Sep. 29, 2014. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

Example 1

Identification of Markers Linked to DM Resistance from *L. Virosa*

A fragment of the *Lactuca virosa* genome, introgressed on Chromosome 7 of *L. sativa*, was associated with broad resistance to DM and fine-mapped to an interval of 49.8-

50.56 cM. This interval appeared to correspond to a physical size of approximately 1,600 Kb. Subsequently, cultivated lettuce lines having resistance to DM obtained from *L. virosa* were subjected to DNA sequencing using the Sanger method. Results were compared to cultivated lettuce lines lacking resistance. The NLSAT009419770 marker (SEQ ID NO: 6) closely linked with DM resistance from *L. virosa* was identified from sequence data, and an assay for plants comprising DM resistance from *L. virosa* was developed.

This marker was shown to be closely linked to DM resistance from *L. virosa*, and no breakage between the marker and the resistance has been observed. The chromosomal segment containing the marker was confirmed to locate on chromosome 7.

Example 2

Characterization of an Introgression from *L. Virosa* on Chromosome 7

Microarray DNA fingerprint data from Crisphead coastal lines exhibiting resistance obtained from *L. virosa* showed an introgression on chromosome 7 in an otherwise cultivated background. The identified introgression was crossed in the seven different types of lettuce using marker-assisted backcrossing (MABC) to test efficacy of the introgression on Chr. 7. Resulting plants maintained the full introgression, and mini-fingerprint data showed that the remaining size of the introgression in these plants was as listed in Table 1. All lines demonstrated resistance, consistent with successful transfer of the introgression from *L. virosa* into distinct genetic backgrounds, exclusively using markers. Crisphead lines comprising the introgression were tested in the field. Butterhead lines exhibiting resistance obtained from *L. virosa* grown in indoor facilities.

TABLE 1

Generation tested and % RP recovered for seven lines comprising an introgression from *L. virosa* conferring resistance to DM.

| Recurrent Parent | Market type | Generation | % RP | Rvir max introgression (cM) |
|---|---|---|---|---|
| Complice | | BC3F3 | 91.4 | 16.94 |
| Lyra | | BC3F3 | 86.5 | 19.40 |
| Zefira | Butterhead, protected culture | BC3F3 | 91.9 | 22.99 |
| Freesol | Oakleaf, open field | BC3F3 | 91.9 | 17.70 |
| Stallion | | BC2F3 | 92.9 | 16.41 |
| PS-6545691 | Crisphead Coastal, open field | BC2F3 | 89.6 | 25.76 |
| RX06413822 | Butterhead, open field | BC2F4 | 93.7 | 22.99 |

Example 3

Recombination Screen in Cultivated Lettuce Comprising an *L. Virosa* Introgression The physical length of the segment comprising the introgression was further investigated using markers and by sequencing small (200-500 bp) fragments in the region. SNPs were identified within each of the 200-500 bp fragments. Using dominant assays, indicative of the absence of elite alleles, it was determined that the introgression started approximately at the physical position of ~53.4 Mb and ended at 56.1 Mb. Physical positions refer to the genome sequence of lettuce, which was generated in a collaboration of the Michelmore lab at UC Davis and the BGI, Shenzen. It was supported by the Lettuce Genome Sequencing Consortium (www.lgr.genomecenter.ucdavis.edu/Home.php).

Figure 1B:
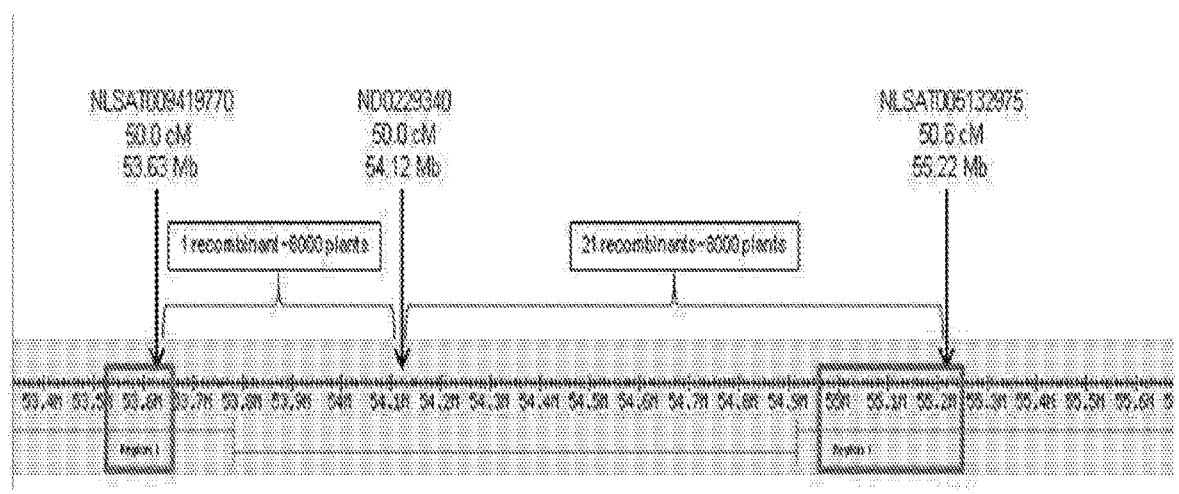

A recombination screen was conducted in order to identify recombination events between three co-dominant markers located within the refined interval. In total, 8000 F2 plants were screened for a recombination event between the three marker assays in the introgression (FIG. 1). Twenty-two recombinants were identified in the screen and grown in the greenhouse to produce seed. Seven recombinants, all of which comprised a recombination event between ND0229340 and NLSAT005132975, did not set seed. The fifteen remaining recombinants were capable of producing seed, and were advanced to further linkage drag evaluation in the field as well as pathology screening to confirm resistance to DM.

Example 4

Pathology Screen of Recombinants

A pathology screen was conducted using 20 seeds of the selfed recombinants tested with *Bremia lactucae* race 27. One recombinant event in line CHCG413-0099, comprising a small introgression of less than 0.0125 cM, corresponding to a segment of approximately 250 kb of *L. virosa* DNA and was still fully resistant to DM.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for selecting a lettuce plant with improved resistance to *Bremia lactucae*, said method comprising detecting in said lettuce plant the presence of a *Lactuca virosa* allele on chromosome 7 that comprises marker locus NLSAT009419770 (SEQ ID NO:6) and confers said resistance to *Bremia lactucae*.

2. The method of claim 1, wherein said lettuce plant is an elite lettuce plant comprising at least one allele from *Lactuca virosa*.

3. The method of claim 1, wherein the lettuce plant is a *Lactuca virosa* plant.

4. A *Lactuca sativa* plant selected by the method of claim 1, wherein the plant comprises a *Lactuca virosa* allele on chromosome 7 that comprises maker locus NLSAT009419770 (SEQ ID NO:6) and confers resistance to *Bremia Lactucae*.

5. The method of claim 1, wherein said method comprises detecting a marker locus in or genetically linked to said *Lactuca virosa* allele on chromosome 7, wherein said marker locus is selected from the group consisting of NLSAT009419770 (SEQ ID NO: 6), ND0229340 (SEQ ID NO: 11), and NLSAT005132975 (SEQ ID NO:1).

* * * * *